United States Patent [19]

Hager

[11] Patent Number: 5,351,532

[45] Date of Patent: Oct. 4, 1994

[54] METHODS AND APPARATUS FOR MAKING CHEMICAL CONCENTRATION MEASUREMENTS IN A SUB-SURFACE EXPLORATION PROBE

[75] Inventor: Robert N. Hager, Spokane, Wash.

[73] Assignee: Paradigm Technologies, Spokane, Wash.

[21] Appl. No.: 960,486

[22] Filed: Oct. 8, 1992

[51] Int. Cl.$^5$ .................. G01N 21/23; E21B 47/00
[52] U.S. Cl. .................. 73/153; 73/61.44; 73/61.48; 250/301; 436/28; 436/29
[58] Field of Search .......... 73/153, 155, 61.43, 73/61.44, 61.48; 250/253, 254, 256, 301, 361 C, 364, 365, 372; 436/25, 28, 29

[56] References Cited

U.S. PATENT DOCUMENTS

| | | | |
|---|---|---|---|
| 2,110,310 | 3/1938 | Shayes et al. | 250/34 |
| 2,206,922 | 7/1940 | Smith | 73/153 |
| 2,263,108 | 11/1941 | Stuart | 250/254 |
| 2,361,261 | 10/1944 | Campbell | 250/253 |
| 2,843,459 | 7/1958 | Meikeljohn | 23/253 |
| 2,973,471 | 2/1961 | Armistead et al. | 175/50 |
| 3,014,529 | 12/1961 | Graham | 175/50 |
| 3,279,249 | 10/1966 | Tocanne | 73/153 |
| 3,524,346 | 8/1970 | Schmidt | 175/50 |
| 3,611,799 | 10/1971 | Davis | 175/50 |
| 3,673,864 | 7/1972 | Cubberly, Jr. | 73/153 |
| 3,710,111 | 1/1973 | Collura | 250/301 |
| 3,776,032 | 12/1973 | Vogel | 73/155 |
| 4,174,629 | 11/1979 | Striegler | 73/153 |
| 4,263,509 | 4/1981 | Fertl et al. | 250/255 |
| 4,293,309 | 10/1981 | Miller | 23/230 |
| 4,370,886 | 2/1983 | Smith, Jr., et al. | 73/153 |
| 4,495,804 | 1/1985 | Le Blanc et al. | 73/152 |
| 4,573,532 | 3/1986 | Blake | 166/264 |
| 4,609,821 | 9/1986 | Summers | 250/254 |
| 4,624,133 | 11/1986 | Iwashita | 250/301 |
| 4,635,735 | 1/1987 | Crownover | 175/48 |
| 4,765,182 | 8/1988 | Boone | 73/153 |
| 4,805,708 | 2/1989 | Matza et al. | 175/40 |
| 4,860,581 | 8/1989 | Zimmerman et al. | 73/155 |
| 4,936,139 | 6/1990 | Zimmerman et al. | 73/155 |
| 4,977,319 | 12/1990 | Supernaw | 250/301 |
| 5,084,617 | 1/1992 | Gergely | 250/253 |
| 5,096,001 | 3/1992 | Buytaert et al. | 175/40 |
| 5,166,747 | 11/1992 | Schroeder et al. | 250/256 |
| 5,239,860 | 8/1993 | Harris et al. | 73/61.48 |

FOREIGN PATENT DOCUMENTS 0004263  1/1980  Japan ................. 73/61.48

OTHER PUBLICATIONS

Fontenot, et al., "MWD can improve well safety, control," Oil & Gas Journal, Technology, Feb. 15, 1988, pp. 40–47.

(List continued on next page.)

Primary Examiner—Hezron E. Williams
Assistant Examiner—Michael Brock
Attorney, Agent, or Firm—Wells, St. John, Roberts, Gregory & Matkin

[57] ABSTRACT

An in-hole oil-drilling probe is mountable in a drill string to measure hydrocarbon concentrations in drilling fluid flowing around the drill string. The probe consists of a drill collar which is mountable in the drill string. A solvent, in which hydrocarbons are soluble, circulates within the drill collar through a hydrocarbon detection chamber. A membrane in the drill collar has an outer surface positioned to contact flowing drilling fluid and an inner surface positioned to contact circulating solvent within the drill collar. The membrane allows hydrocarbons to permeate from the drilling fluid into the solvent and into the hydrocarbon detection chamber with the solvent. A radiant energy source directs radiant ultra-violet energy into the hydrocarbon detection chamber. A sensor apparatus measures fluorescent energy radiating from the hydrocarbon detection chamber to determine solvent hydrocarbon concentration. The sensor apparatus preferably comprises a pair of sensors which are responsive to two different energy wavelengths, respectively, to discriminate from hydrocarbons originating from sub-surface fluids and hydrocarbons (primarily diesel oil) originating from drilling fluid.

27 Claims, 7 Drawing Sheets

OTHER PUBLICATIONS

Rao et al., "MWD gains as formation-evaluation tool," Oil & Gas Journal, Feb. 8, 1988, Technology, pp. 44-48.

Fontenot, et al., "MWD aids vital drilling decisions," Oil & Gas Journal, Mar. 14, 1988, Technology, pp. 60-65.

Burgess, et al., "Advances in MWD technology improve real time data," OGJ Special, Feb. 17, 1992. Oil & Gas Journal, pp. 51-61.

University of Wyoming NEWS, "Remote Sensor Device Developed For Groundwater Research," May 21, 1992.

Fontenot, "Measurement while-drilling essential to drilling," Oil & Gas Journal, Technology, March 28, 1988 pp. 52-55.

McGown et al., "Molecular Fluorescence, Phosphorescence, and Chemiluminescence Spectrometry," Analytical Chem. vol. 62, No. 12, Jun. 15, 1990, pp. 255R-267R.

"Technology rescues the Oil Patch," Design News, Jun. 25, 1990, pp. 25-26.

Hall, "Measurement While Drilling," FirstBoston--Equity Research, Jul. 31, 1991, pp. 1-14.

Rao, et al., "Many factors determine need for real-time or recorded data," Oil & Gas Journal, Technology, Jan. 25, 1988, pp. 65-69.

Calhoun, et al., "Surface fluorescence method can identify potential oil pay zones in Permian Basin," Oil & Gas Journal, Sep. 26, 1992, pp. 96-100.

METHODS AND APPARATUS FOR MAKING CHEMICAL CONCENTRATION MEASUREMENTS IN A SUB-SURFACE EXPLORATION PROBE

TECHNICAL FIELD

This invention relates to systems and methods for performing real-time measurements of chemical concentrations in sub-surface earth formations.

BACKGROUND OF THE INVENTION

Many improvements have been made in oil-drilling technology in the past two decades. As a result, operators are able to drill faster, deeper, and longer. Along with these capabilities, however, have come greater costs and greater needs for efficiency.

Oil exploration is performed by drilling test holes using an oil-drilling bit connected at the lower end of a drill string. Technological advances now allow advanced directional and horizontal drilling, using steerable drilling systems. However, the ability to steer an oil-drilling bit necessitates that the desired path of the drilling be continually reevaluated. Other drilling parameters, dictated by considerations of varying complexity, must also be specified as drilling proceeds. Many decisions affecting drilling operations are based on physical properties of formations within the bore hole. Knowledge of these physical properties is also used to determine reservoir properties and capacities. In short, an accurate knowledge of bore hole conditions allows an operator to determine whether he is drilling in the right place. The sooner the operator receives this knowledge, the more efficient will be his decisions regarding drilling activities.

When searching for hydrocarbon-bearing sub-surface earth formations, many drilling path decisions and other decisions relating to drilling activities are most desirably based on the actual hydrocarbon content of encountered sub-surface formations. At one time, the primary technique for determining hydrocarbon content was to analyze actual core samples taken from the sides of the bore hole itself after drilling. Hydrocarbon measurements, made directly upon these samples, resulted in direct and seemingly highly reliable data.

This technique, although still in use, has been found to be less accurate under some conditions than had previously been thought. For instance, by the time core samples are taken, hydrocarbon-bearing fluids initially contained therein may have been lost or diluted. In addition, core samples are often not representative of the sub-surface rock formation as a whole.

More recently, so called "wire" or "wireline" logging has been used to make indirect measurements of physical properties in a bore hole. Wireline logging involves withdrawing the drill string and then lowering a data-logging instrument by wire or cable into the open bore hole. A wireline logging instrument performs various measurements as a function of depth, including, for example, bore hole diameter, electrical potential between formation beds, radioactive impurities in the formation, and electrical resistivity. Hydrocarbon concentrations are inferred from this information.

The primary disadvantage of wireline logging is that, to date, these instruments are incapable of making direct hydrocarbon measurements. Rather, hydrocarbon content must be inferred from the measurements noted above. A further disadvantage is that measurements may be affected by drilling fluids which fill the bore hole.

Both of the above methods suffer from the additional disadvantage that measurement results are delayed for a significant time after the drilling bit has encountered specific formations. In addition, the measurements are performed only at discrete, and rather lengthy, time intervals, and require drill string withdrawal. The delayed and discrete nature of the measurements limits an operator's ability to respond quickly to changing bore hole conditions, since many such conditions will become known to the operator, if at all, only after the drilling bit has passed the point where the conditions were encountered.

Another notable technique for determining in-hole hydrocarbon concentrations is that of "mud logging." In mud logging, drilling fluid, often called drilling mud, is analyzed for hydrocarbon content. Drilling mud is a water-based fluid which is pumped through the drill string to the drill bit during drilling. The mud then rises upward around the drill string to carry cuttings and fluids encountered by the drilling bit to the surface. Mud samples are collected as the mud reaches the top of the bore hole. Gases are withdrawn from the mud samples and analyzed by a conventional gas chromatograph technique for presence of hydrocarbons. The hydrocarbon content of the mud reaching the surface is correlated to the depth at which the mud emerged from the drill string to determine hydrocarbon content at that depth.

While mud logging provides accurate measurements of hydrocarbons occurring in the drilling mud, these measurements do not always correspond to the actual hydrocarbon content of encountered sub-surface formations. For one thing, drilling mud itself, as injected into the bore hold, often contains hydrocarbons such as diesel oil which must be accounted for. In addition, as the drilling mud rises through the bore hole it accumulates hydrocarbons from previously-encountered sections of the bore hole. It is not always possible to predict or account for this accumulation in relation to the hydrocarbons originating from the bottom of the bore hole. Furthermore, concentrations of hydrocarbons actually originating from the bottom of the bore hole are often dispersed and diluted by the time the drilling mud reaches the surface.

Another problem with mud logging is that measurements are often delayed more than thirty minutes from the time the drilling bit actually encounters a specific hydrocarbon formation. This is the time required for the drilling mud to rise around the drill string to the surface. Additional time is often consumed in de-gassing and performing actual measurements on the drilling mud. While the delay is not as serious as with the previously-mentioned techniques, it is still of concern to an operator faced with critical decisions regarding drilling paths and other parameters.

Measurement While Drilling (MWD) technology provides real-time information regarding bore hole physical properties near the drilling bit during actual drilling. The first commercially feasible MWD sensors reached the market in the early 1970's, and were concerned primarily with drill guidance, where real-time information is imperative. Since then, however, MWD sensors have been developed for making a variety of formation measurements.

MWD instruments are located within specially designed drill collars near the drill bit at the base of the drill string. The instruments take various samples during the drilling process, and the information gathered may be stored in downhole memories and/or transmitted to the surface via acoustic pulses in the drilling mud. Power is provided either by internal batteries or by power turbines driven by flowing drilling mud.

To date, MWD instruments provide geological data on downhole formations much like wireline logging, except that the data is provided on a continuous basis in real time. This data may be used both to enhance overall drilling efficiency and to evaluate hydrocarbon production potential of the formations encountered. Resistivity and gamma measurements, from which hydrocarbon concentrations can be inferred, are the primary means of evaluating drilling efficiency when using MWD systems.

At this time, however, there are no commercially available MWD probes for making direct and continuous measurements of hydrocarbon concentrations at the base of the bore hole. One reason for the absence of such a sensor is the extremely harsh environment in which MWD instruments must operate, resulting primarily from the fact that the sensors have to be placed in a drilling bottom-hole assembly. The instruments must therefore provide measurements in an environment that is hostile from the standpoint of pressure, vibration, shock, flow, and the presence of cuttings. Additionally, all of the instruments must be housed in a small space while not impairing the mechanical integrity of the drill string assembly.

In spite of the harsh environment, reliability of MWD sensors is a critical issue. The cost of prematurely withdrawing a drill string to repair or replace a malfunctioning MWD sensor is very high.

Accordingly, there is a definite need for a device which provides continuous and real time hydrocarbon measurements at the base of a bore hole during drilling.

BRIEF DESCRIPTION OF THE DRAWINGS

Preferred embodiments of the invention are described below with reference to the accompanying drawings.

DETAILED DESCRIPTION OF THE PREFERRED EMBODIMENT

This disclosure of the invention is submitted in furtherance of the constitutional purposes of the U.S. Patent Laws "to promote the progress of science and useful arts." U.S. Constitution, Article 1, Section 8.

In accordance with a preferred embodiment of the invention, described below is a sub-surface exploration probe for making repeated and real-time concentration measurements of a chemical occurring in a sub-surface fluid. The probe comprises:

- a probe housing having a surface which is exposed to the sub-surface fluid;
- a chemical detection chamber for containing a solvent in which the chemical is soluble;
- a filter having a first side positioned relative to the probe housing to contact the sub-surface fluid, the filter having a second side positioned relative to the probe housing to contact solvent within the housing, the filter allowing the chemical to permeate from the sub-surface fluid into solvent within the housing;
- a radiant energy source positioned relative to the chemical detection chamber to direct radiant energy into the chemical detection chamber; and
- a sensor positioned relative to the chemical detection chamber to measure radiant energy within the chemical detection chamber and thereby determine solvent chemical concentration.

Figure 1:
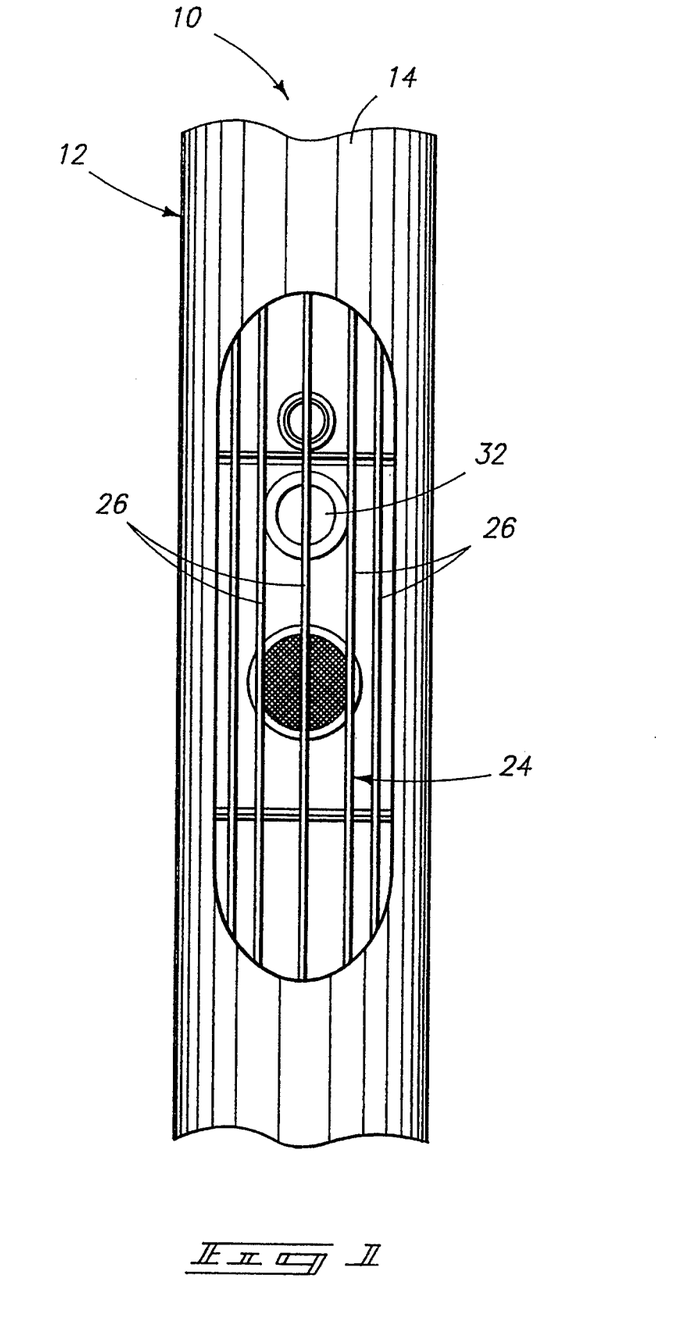
FIG. 1 is a front elevational view of a sub-surface exploration probe in accordance with a preferred embodiment of the invention.

More specifically, FIG. 1 shows a sub-surface exploration probe or in-hole measurement-while-drilling (MWD) oil-drilling probe 10 in accordance with a preferred embodiment of the invention. Oil-drilling probe 10 is utilizable for making repeated real-time concentration measurements, while drilling, of a selected chemical occurring in a sub-surface fluid such as drilling mud or fluid. Oil drilling probe 10 is mountable in a drill string (not shown) to measure selected hydrocarbon concentrations in drilling fluid flowing around the drill string.

Oil-drilling probe 10 includes a probe housing having a surface which is exposed to the sub-surface fluid to be analyzed. The probe housing comprises a drill collar 12 which is mountable in the drill string to rotate therewith. Drill collar 12 has a cylindrical outer surface 14 centered about a vertically-oriented longitudinal axis. Drill collar 12 is adapted to join with drill string components near the bottom of the drill string, in close proximity to a drill bit (not shown). Drilling mud or fluid is pumped down through the interior of drill collar 12 to the drill bit, as described below, and then rises around the drill string, carrying with it cuttings and fluids encountered by the drill bit. Outer surface 14 is thus is exposed to drilling mud during drilling.

Figure 2:
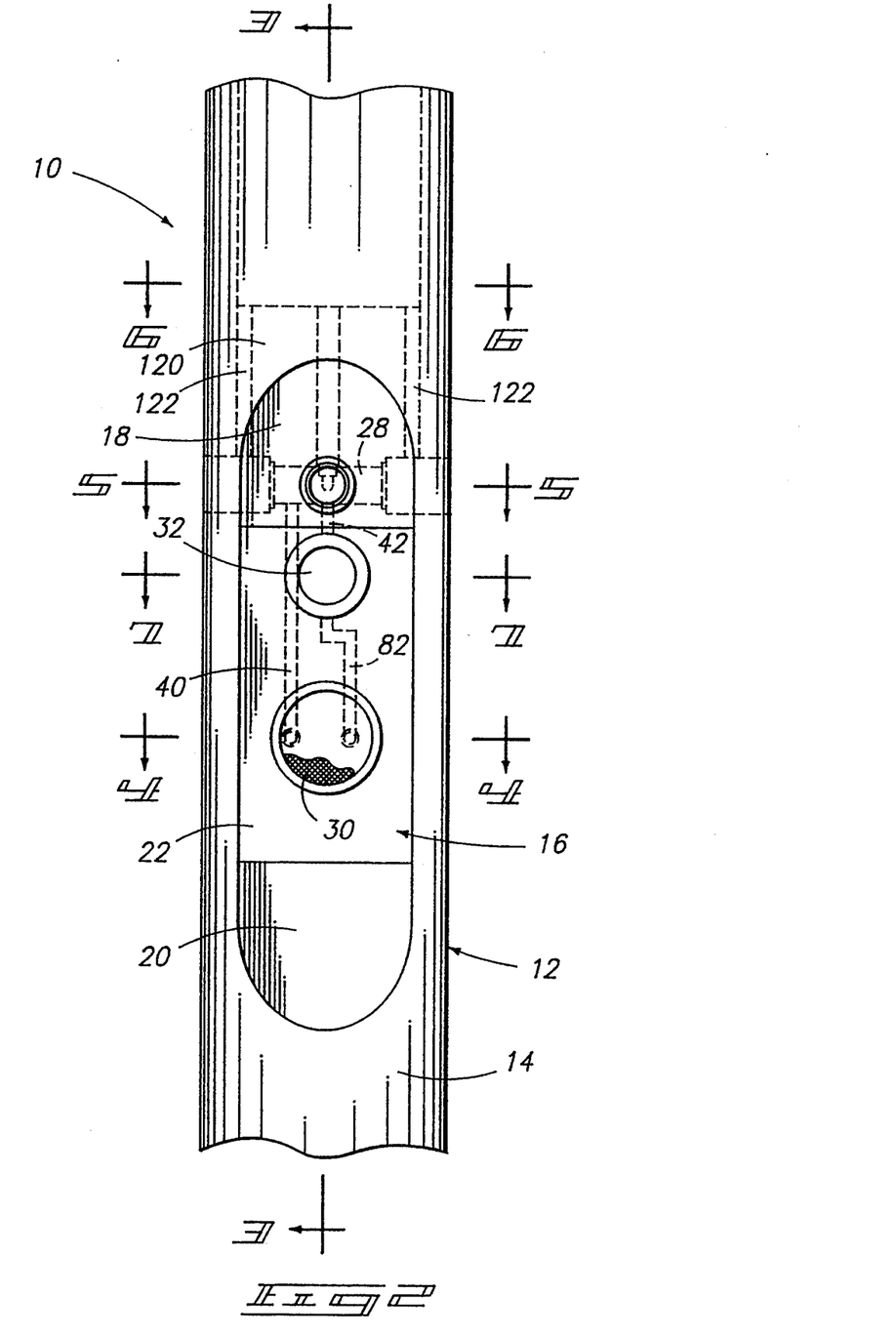
FIG. 2 is a front view of the sub-surface exploration probe of FIG. 1, shown with a protective grill removed.
Figure 3:
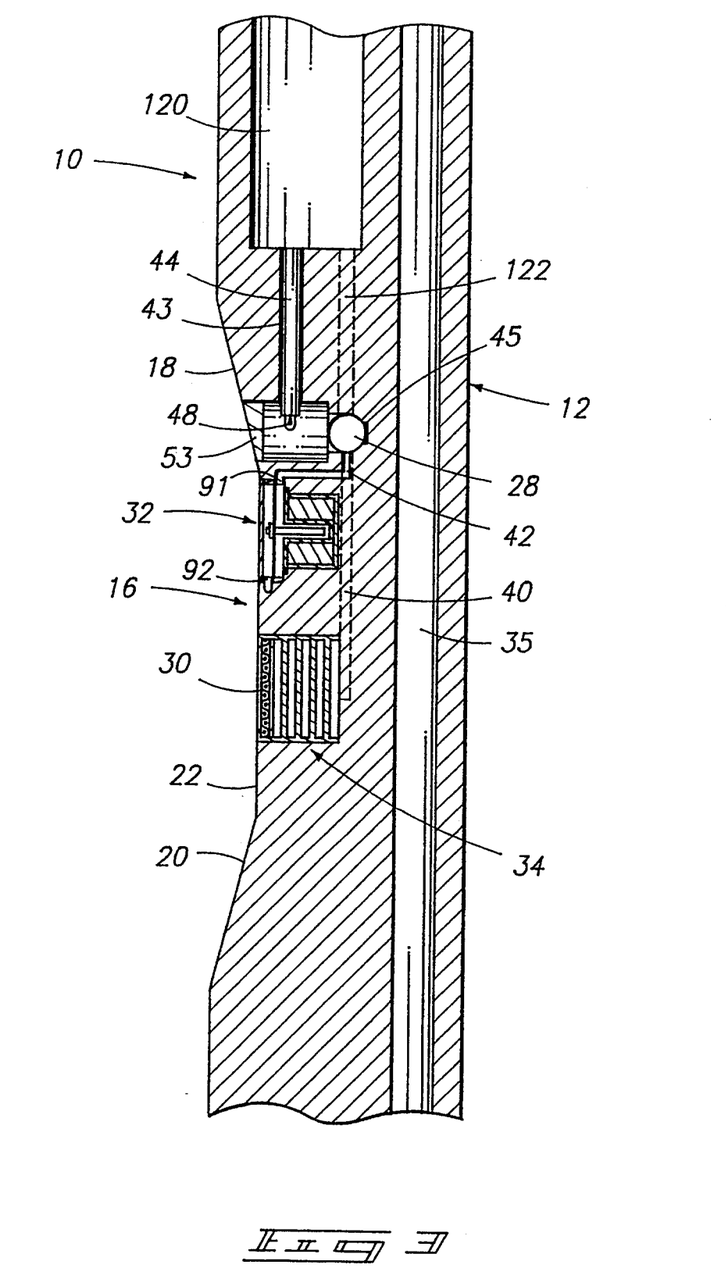
FIG. 3 is a cross-sectional side view of the sub-surface exploration probe of FIG. 1, taken along line 3—3 of FIG. 2.

Referring to FIGS. 2 and 3, a notch or recess 16 is formed along drill collar 12 behind or inward from outer surface 14. Recess 16 forms upper and lower tapering recessed surfaces 18 and 20 and a central recessed surface 22. Each of these surfaces is planar, with central recessed surface 22 being parallel to the longitudinal axis of drill collar 12. Upper and lower recessed surfaces 18 and 20 are inclined from central recessed surface 22 to intersect outer surface 14.

A protective grill 24 (shown only in FIG. 1) is removably mounted within recessed portion 16. Protective grill 24 has a plurality of ribs 26 which extend vertically along the length of recess 16. Ribs 26 form a plurality of vertically extending slots which allow drilling mud to pass next to the surfaces of recess 16 while preventing larger sub-surface objects such as rocks or other solid fragments from contacting such surfaces. The outer profile of grill 24 is curved to correspond to the cylindrical outer surface 14 of drill collar 12. Grill 24 preferably includes a cover (not shown) formed partially over ribs 26 to form a duct over central recessed surface 22. Drilling fluid passes inward through ribs 26 adjacent lower recessed surface 20, upward along central recessed surface 22 beneath the cover, and outward through ribs 26 adjacent upper recessed surface 18. Protective grill 24 is removable to allow access to probe components described below.

Oil-drilling probe 10 includes a chemical or hydrocarbon detection chamber 28, a membrane filter 30, a solvent pump 32 and a chemical absorption chamber 34. These elements are generally mounted or arranged within drill collar 12 behind recess 16 for fluid communication with each other.

In addition, a drilling fluid passage 35 extends vertically along the entire length of drill collar 12 to communicate fresh drilling fluid through drill collar 12 to the bottom of the drill string. After exiting the drill string near the drill bit, drilling fluid rises around drill collar 12, contacting outer surface 14 of drill collar 12 and recessed surfaces 18, 20, and 22 of recess 16.

Solvent pump 32 circulates a selected chemical or hydrocarbon solvent within drill collar 12 through chemical absorption chamber 34 and hydrocarbon detection chamber 28, and behind membrane filter 30. The solvent is chosen to selectively dissolve the chemical to be measured. In the preferred embodiment described herein, the solvent comprises ethanol, a weak solvent to hydrocarbons. Ethanol is capable of dissolving a small fraction of hydrocarbons present in drilling fluid, without significantly dissolving other elements which are also present in the drilling fluid. If chemicals other than hydrocarbons are to be measured, the solvent must be chosen to dissolve those chemicals. While a weak solvent is preferable when measuring hydrocarbons, a stronger solvent may be required in other cases, especially in cases where there is a very weak concentration of the chemical of interest.

Figure 4:
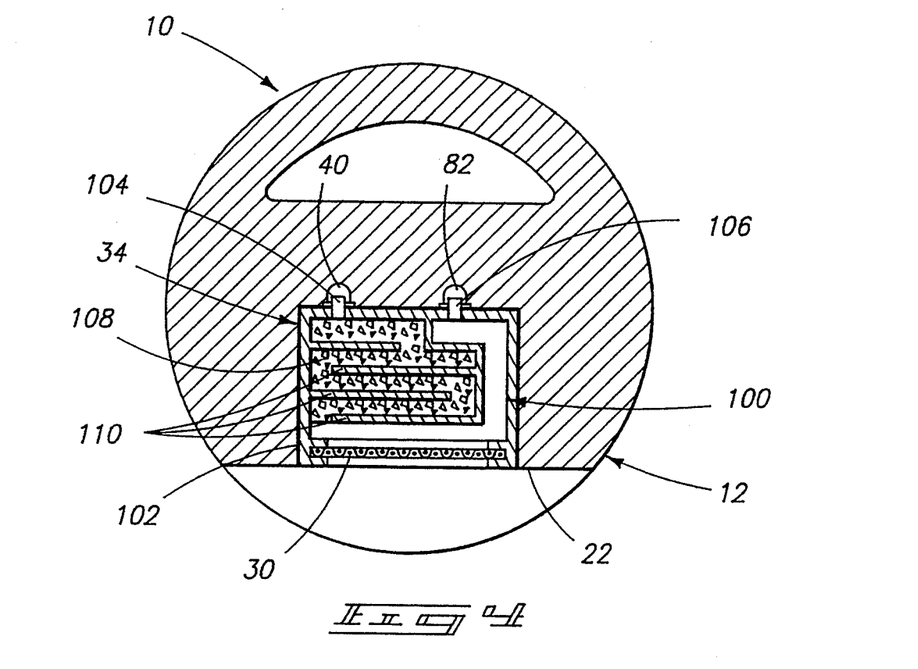
FIG. 4 is an enlarged cross-sectional view of the sub-surface exploration probe of FIG. 1, showing a chemical absorption chamber, taken along line 4—4 of FIG. 2.
Figure 8:
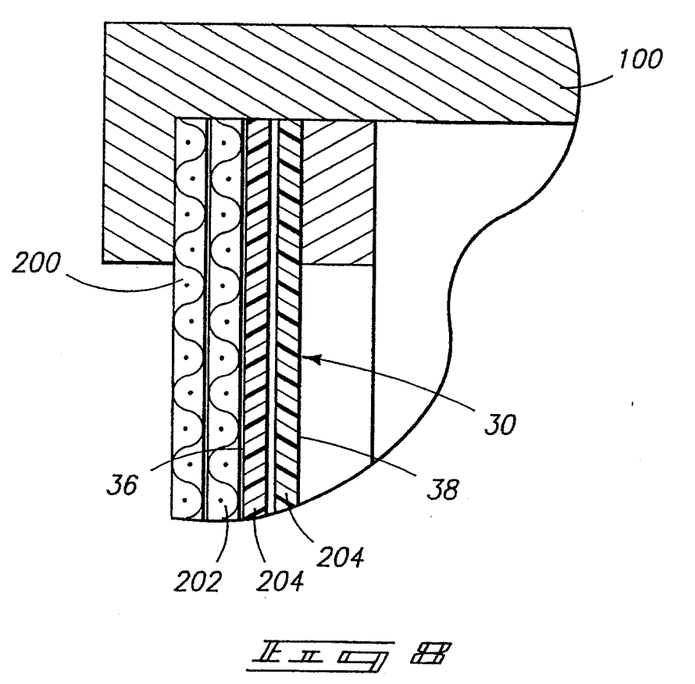
FIG. 8 is an enlarged cross-sectional view showing a membrane filter of the sub-surface exploration probe of FIG. 1.

Referring to FIGS. 4 and 8, membrane filter 30 is positioned along central recessed surface 22 to contact both drilling fluid and solvent, allowing solvent within drill collar 12 to contact drilling fluid and to dissolve hydrocarbons from the drilling fluid into the solvent. More specifically, membrane filter 30 has a first or outer side or surface 36 positioned relative to drill collar 12 to contact drilling fluid. Membrane filter 30 has a second or inner side or surface 38 positioned relative to drill collar 12 to contact solvent within drill collar 12. Solvent pump 32 continuously circulates solvent along inner surface 38. Membrane filter 30 allows hydrocarbons to permeate or pass therethrough from drilling fluid into the circulating solvent.

Membrane filter 30 is selected to allow hydrocarbons or other chemicals of interest to permeate from the drilling fluid into the solvent. Specifically, membrane filter 30 comprises a polymer material such as nylon, and preferably one or more nylon membranes 204. Membranes 204 are protected by a pair of wire mesh screens 200 and 202 adjacent outer surface 36. Outermost mesh screen 200 has a relatively coarse, number eight mesh size. It is intended to prevent larger sized objects from contacting nylon membranes 204. Innermost mesh screen 202 has a relatively fine, number 100 mesh size. It is intended to prevent even small objects from contacting and possibly clogging nylon membranes 204. Nylon membranes 204 themselves have a very small pore size of about 0.1 microns, and for the most part prevent passage of any particulate matter. Nylon membranes such as those described are available from Whatman International, Ltd. of Maidstone, England (Cat #7401-004).

Mesh screens 200 and 202 are intended primarily to prevent clogging of nylon membranes 204, while also providing a degree of physical protection against external objects which might otherwise puncture nylon membranes 204. While it might also seem desirable to also place such screen along inner surface 38 of membrane filter 30 to provide physical strength to membrane filter 30, doing so has been found to have a detrimental effect on the useful life of nylon membranes 204. The reason for this is the frequent pressure transients produced by the drilling fluid within a borehole. These transients are often as high as 1000 p.s.i., occurring in as little as 50 milliseconds. Such pressure transients crease or otherwise damage nylon membranes 204 if backed along inner surface 38 by a screen or other type of support. Surprisingly, nylon membranes 204 have much longer lives if left unsupported along their inner surfaces. Apparently, the natural flexibility of nylon membranes 204 allows them to absorb the relatively large pressure transients without damage.

In operation, nylon membrane 204 filters particulates from the drilling fluid while allowing dissolved hydrocarbons to pass therethrough. A small amount of solvent will eventually be lost into the drilling fluid, and the remaining solvent will eventually become diluted with fluids which enter from outside drilling collar 12. However, the rate of such loss and dilution is so slow as to have little or no practical significance, since solvent will typically be replaced at periodic intervals. The flexible nature of membrane filter 30 equalizes the pressure of the drilling fluid and the solvent, thereby minimizing forced migration of fluids into drill collar 12.

It is contemplated that the mechanical filtration presently employed by membrane filter 30 could be replaced in some situations by a filter which is chemical acting. Such a filter would be chosen to pass selected chemicals of interest while blocking others.

Figure 5:
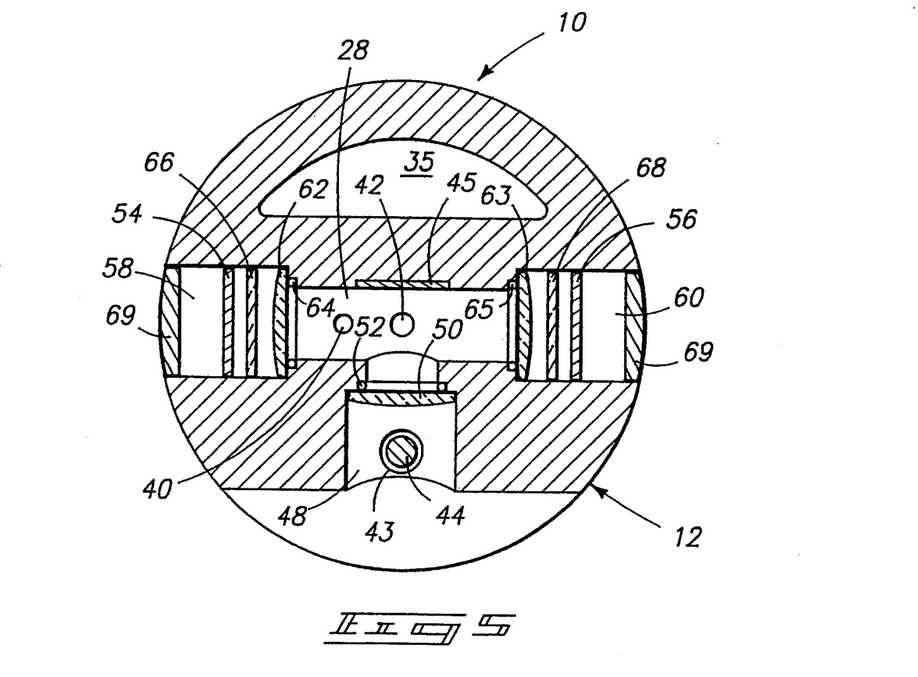
FIG. 5 is an enlarged cross-sectional view of the sub-surface exploration probe of FIG. 1, showing a hydrocarbon detection chamber, taken along line 5—5 of FIG. 2.

Referring now to FIGS. 2, 3, and 5, solvent circulates into and passes through hydrocarbon detection chamber 28 after passing behind membrane filter 30. Solvent enters hydrocarbon detection chamber 28 through a solvent passage 42 from solvent pump 32. Hydrocarbon detection chamber 28 is a generally cylindrical bore extending horizontally behind and parallel to central recessed surface 22. Hydrocarbon detection chamber 28 contains the solvent while the solvent is analyzed for hydrocarbon concentration by fluorescent spectroscopy. Solvent leaves hydrocarbon detection chamber 28 through a solvent passage 40 to chemical absorption chamber 34.

Oil drilling probe 10 includes means for transmitting radiant energy into the solvent within hydrocarbon detection chamber 28. Such means comprises a radiant energy source 44 (FIG. 5) within a lamp chamber 48. Lamp chamber 48 comprises a cylindrical bore which extends horizontally from upper recessed surface 18 to intersect hydrocarbon detection chamber 28 at a right angle. A vertically-extending lamp bore 43 extends upward from lamp chamber 48. Radiant energy source 44 is received within lamp bore 43, positioned to direct radiant energy into hydrocarbon detection chamber 28. Lamp chamber 48 also contains a lens 50 which seals against an O-ring 52 to isolate hydrocarbon detection chamber 28 from lamp chamber 48. Lens 50 gathers radiant energy from radiant energy source 44 and concentrates it within hydrocarbon detection chamber 28. A removable opaque plug 53 (FIG. 3) seals lamp chamber 48 from the outside environment while allowing access to lamp chamber 28 as needed.

Radiant energy source 44 is preferably a penlight-sized ultraviolet lamp having an operative end from which ultraviolet light is emitted. More specifically, radiant energy source 44 is a miniature UV lamp such as Catalog No. L6070-6 available from Baxter Scientific Products Division. This lamp emits narrow-bandwidth UV energy at 254 nanometers. This wavelength has been found to excite fluorescence in hydrocarbons such as those encountered in sub-surface drilling.

To provide additional stimulus for fluorescence, a mirror 45 is optionally positioned within or relative to hydrocarbon detection chamber 28 opposite radiant energy source 44. Mirror 45 reflects radiant UV energy passing through hydrocarbon detection chamber 28 from radiant energy source 44, resulting in two passes of UV light through hydrocarbon detection chamber 28.

It is contemplated that direct absorption spectroscopy techniques could replace the florescence techniques described. For instance, a lamp could introduce radiation at a specific wavelength or range of wavelengths into the hydrocarbon detection chamber, and the reduction in intensity of this radiation then measured by one or more sensors to determine the concentration of absorbing chemical in the solvent.

Oil-drilling probe 10 also comprises means for measuring radiant fluorescent light energy or intensity emanating from the solvent within hydrocarbon detection chamber 28 and for determining drilling fluid hydrocarbon concentration based on the measured radiant energy from the solvent. Such means comprises a sensor apparatus positioned relative to hydrocarbon detection chamber 28 to measure radiant energy within hydrocarbon detection chamber 28 and to thereby determine chemical or hydrocarbon concentrations within the solvent. The sensor apparatus comprises first and second sensors 54 and 56 positioned relative to hydrocarbon detection chamber 28 to measure fluorescent light intensity from hydrocarbons in hydrocarbon detection chamber 28 at two different center wavelengths. These sensors are preferably silicon photodiodes such as those available from Oriel Corporation of Stratford, Conn., under the model designation 71831.

Sensor housings 58 and 60 extend between either transverse end of hydrocarbon detection chamber 28 and outside surface 14 of drill collar 12. Sensor housings 58 and 60 are cylindrical bores which are coaxial with the cylindrical bore forming hydrocarbon detection chamber 28, having a slightly larger diameter than that of hydrocarbon detection chamber 28.

First and second sensors 54 and 56 are positioned within sensor housings 58 and 60, respectively. Lenses 62 and 63 are positioned between sensors 54 and 56 and hydrocarbon detection chamber 28, and are sealed against O-rings 64 and 65 to isolate sensor housings 58 and 60 from hydrocarbon detection chamber 28. In addition, first and second optical filters 66 and 68 are positioned relative to sensors 54 and 56, respectively, to filter radiant energy reaching first and second sensors 54 and 56 and to pass radiant energy resulting from fluoresced energy from the solvent in hydrocarbon detection chamber 28. A pair of opaque removable plugs 69 seal sensor housings 58 and 60 from the external environment surrounding drill collar 12.

Optical filtering is employed to discriminate or differentiate between fluorescence of hydrocarbons originating from sub-surface fluids and hydrocarbons originating from the drilling fluid. Hydrocarbons are known to fluoresce at a number of wavelengths. In addition, different hydrocarbons have different fluorescence characteristic at different wavelengths. Accordingly, it is possible to differentiate between hydrocarbons by comparing their fluorescence at one or more wavelengths. When two hydrocarbons are present in the same sample, the approximate ratio of the two hydrocarbons can be determined by comparing fluorescence of the sample at first and second wavelengths. The first and second wavelengths are different from each other to correspond to peak fluorescence wavelengths of the two hydrocarbons of interest.

Optical filters 66 and 68 are chosen to determine whether fluorescence is due to hydrocarbons originating from the bore-hole or hydrocarbons (primarily diesel oil) originating from the drilling fluid itself. Typical in-hole hydrocarbons found in crude oil have been found to respond to an excitation wavelength of 254 nanometers by fluorescing in a band centered at 360 nanometers. Diesel oil hydrocarbons similarly respond to the same excitation wavelength by fluorescing in a band centered at 320 nanometers. The two fluorescence bands overlap, so that fluorescence at each center wavelength can be due to hydrocarbons either from in-hole crude oil or from diesel oil. Determining the actual source of the fluorescence is therefore impossible when measuring at only a single wavelength. However, taking the ratio of measurements at the two center wavelengths has been found to accurately determine the source of fluorescence.

Accordingly, optical filters 66 and 68 have pass-band center wavelengths corresponding to 320 and 360 nanometers. Optical filters 66 and 68 are positioned between hydrocarbon detection chamber 28 and sensors 54 and 56 to filter radiant energy other than that which results from fluorescence of hydrocarbons in the solvent. This allows sensors 54 and 56 to measure only radiant energy resulting from hydrocarbon fluorescence. Optical filters 66 and 68 are conventional UV filters such as available from Oriel Corporation of Stratford, Conn. They preferably have a narrow pass bandwidth of approximately 10 nanometers.

Determining hydrocarbon concentration in the solvent therefore comprises measuring fluoresced UV light intensity from the solvent within hydrocarbon detection chamber 28 at two differing center wavelengths. Determining hydrocarbon concentration also includes the further step of comparing or ratioing the measured light intensities at the two center wavelengths to discriminate between hydrocarbons originating from sub-surface fluids and hydrocarbons originating from the drilling fluid. Specifically, oil drilling probe 10 divides measured UV intensity at the wavelength corresponding to crude oil hydrocarbons to the measured intensity at the wavelength corresponding to diesel oil hydrocarbons. If this ratio is less than one, it is concluded that fluorescent emissions are due to drilling fluid hydrocarbons such as diesel oil. The presence of in-hole or crude oil hydrocarbons is indicated by a ratio of over unity. Different wavelengths and threshold ratios are chosen to discriminate between other types of chemicals.

In practice, radiant energy source 44 is pulsed on and off at about one cycle per second. This allows determination of reference voltages for sensors 54 and 56 and their associated electronics, as further described below with reference to FIG. 9.

Figure 7:
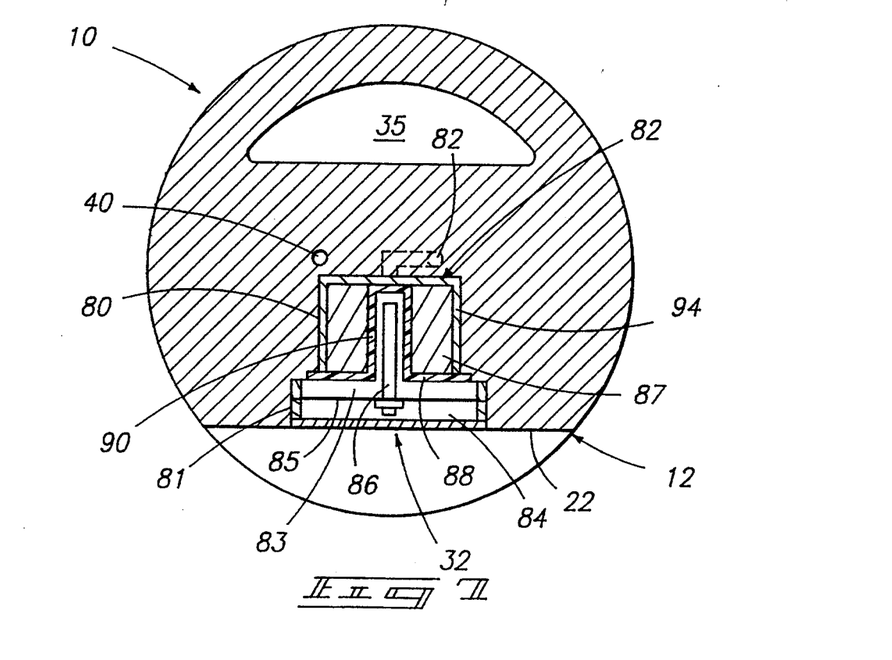
FIG. 7 is an enlarged cross-sectional view of the sub-surface exploration probe of FIG. 1, showing a solvent pump, taken along line 7—7 of FIG. 2.

Referring now to FIGS. 3 and 7, solvent pump 32 is housed within a pump housing 80 formed within drill collar 12 behind central recessed surface 22 of recess 16. Pump housing 80 is in fluid communication with hydrocarbon detection chamber 28 through solvent passage 42, and with chemical absorption chamber 34 through another solvent passage 82.

Solvent pump 32 comprises a cylindrical outer pump section 81 and a coaxial cylindrical inner pump section 94 of reduced diameter. Pump housing 80 is complementary in shape to solvent pump 32. Solvent pump 32 is thus removably received within pump housing 80, with the outer pump section 81 of solvent pump 32 being approximately flush with central recessed surface 22 of recess 16. Outer pump section 81 is bisected into outlet and inlet chambers 83 and 84 by a flexible mylar diaphragm 85. Diaphragm 85 has an attached steel armature 86 which extends from the center of diaphragm 85 toward and into inner pump section 94. Inner pump section 94 contains a cylindrical electrical coil 87 which surrounds steel armature 86. An isolation member 88 is positioned between inner pump section 94 and outer pump section 81, having a central tube 90 which extends coaxially into inner pump section 94 within coil 87. Armature 86 is received within tube 90. Isolation member 88 prevents solvent from contacting coil 87. Inlet chamber 84 communicates with solvent passage 82 through an inlet aperture and check valve 92 (FIG. 3) positioned in the wall of outer pump section 81. Outlet chamber 83 communicates with solvent passage 42 through an outlet aperture 91 (FIG. 3). Steel armature 86 is hollow, having apertures on either side of mylar diaphragm 85 to allow fluid passage therebetween. A check valve within armature 86 (not shown) ensures that fluid flow is only in the direction from inlet chamber 84 to outlet chamber 83.

In operation, electric coil 87 is driven with an approximately 60 Hz alternating current. Coil 87 produces a varying or oscillating magnetic field which oscillates or drives armature 86 through a displacement of about 1/16″. This reciprocation causes the apparatus to slowly pump solvent within the interior of drill collar 12. Specifically, solvent is pumped from solvent pump 32, through solvent passage 42 to hydrocarbon detection chamber 28, through solvent passage 40 to chemical absorption chamber 34, and through solvent passage 82 back to solvent pump 32.

FIG. 4 shows chemical absorption chamber 34 in detail. Solvent pump 32 circulates solvent through chemical absorption chamber 34 to remove hydrocarbons from the solvent after fluorescent spectroscopy. Chemical absorption chamber 34 comprises a cylindrical module or insert 100 which is removably received within a cylindrical bore formed behind and perpendicular to central recessed surface 22 of recess 16. Chemical absorption chamber 34 has a cylindrical outer wall 102 complementary in diameter to the cylindrical bore. Chemical absorption chamber 34 has a pair of fluid ports 104 and 106 for ingress and egress of solvent. Fluid ports 104 and 106 preferably comprise protruding nipples which mate with and seal against corresponding receptacles formed in drill collar 12 to communicate with solvent passages 40 and 82.

Solvent enters chemical absorption chamber 34 through fluid port 104. Entering solvent has dissolved hydrocarbons which are removed in chemical absorption chamber 34 by a bed of activated charcoal 108 contained therein. Activated charcoal purchased from Supelco, of Bellefont, Pa. (Cat. #2-2451), has been found to provide superior performance, although there are many other sources of acceptable activated charcoal. The activated charcoal is contained within a series of baffles 110 which route the solvent slowly through an extended path through chemical absorption chamber 34. Alternatively, baffles 110 can be replaced with a series of thin disks. Each disk has small holes either on its outer periphery of near its center. Such disks are located alternately adjacent each other, with activated charcoal therebetween, such that fluid is forced to first flow radially outward and then radially inward through the activated charcoal to traverse the series of disks.

Activated charcoal 108 removes the hydrocarbons from the solvent. After the hydrocarbons are removed, the solvent is circulated behind inner surface 38 of membrane filter 30 and then out fluid port 106 to solvent pump 32 and hydrocarbon detection chamber 28.

Figure 6:
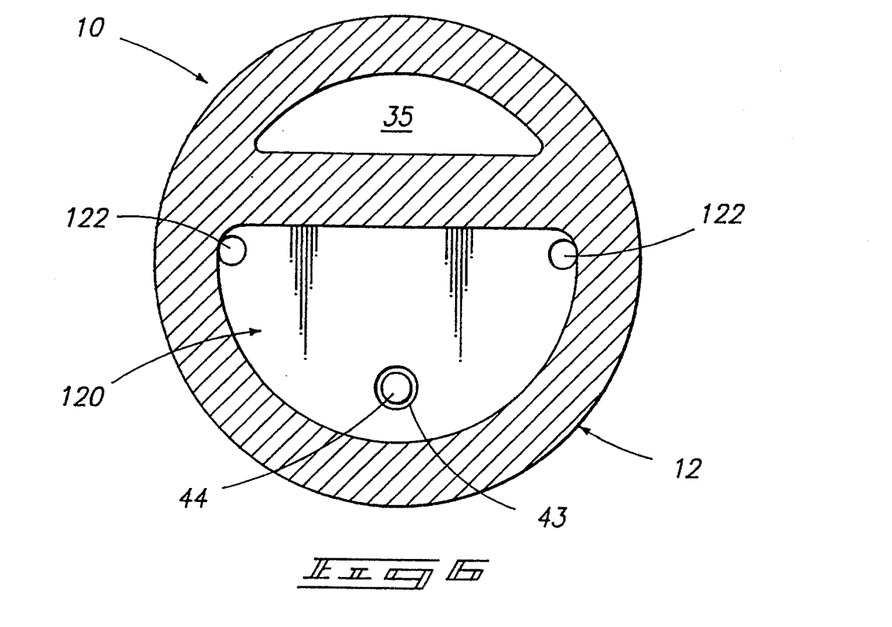
FIG. 6 is an enlarged cross-sectional view of the sub-surface exploration probe of FIG. 1, showing an electronics housing, taken along line 6—6 of FIG. 2.

Referring now to FIG. 6, in-hole oil-drilling probe 10 includes an electronics compartment 120 in drill collar 12 above hydrocarbon detection chamber 28. Electronics compartment 120 is indicated in FIG. 2 by dashed lines. FIG. 6 shows a cross-section of drill collar 12, showing the bottom of electronics compartment 120. A pair of sensor wire apertures 122 extend vertically between electronics compartment 120 and sensor housings 58 and 60. Leads (not shown) extend from sensors 54 and 56 through sensor wire apertures 122, and into electronics compartment 120. In addition, radiant energy source 44 extends upward through lamp bore 43, having leads which also extend into electronics compartment 120.

Electronics compartment 120 contains necessary electronic devices, preferably including processing means, for operating the various electrical and electronic components described above and for performing the described measurements and calculations. Power is supplied either by a battery within electronics compartment 120, a small turbine powered by drilling fluid flowing within drilling fluid passage 35, or both.

Figure 9:
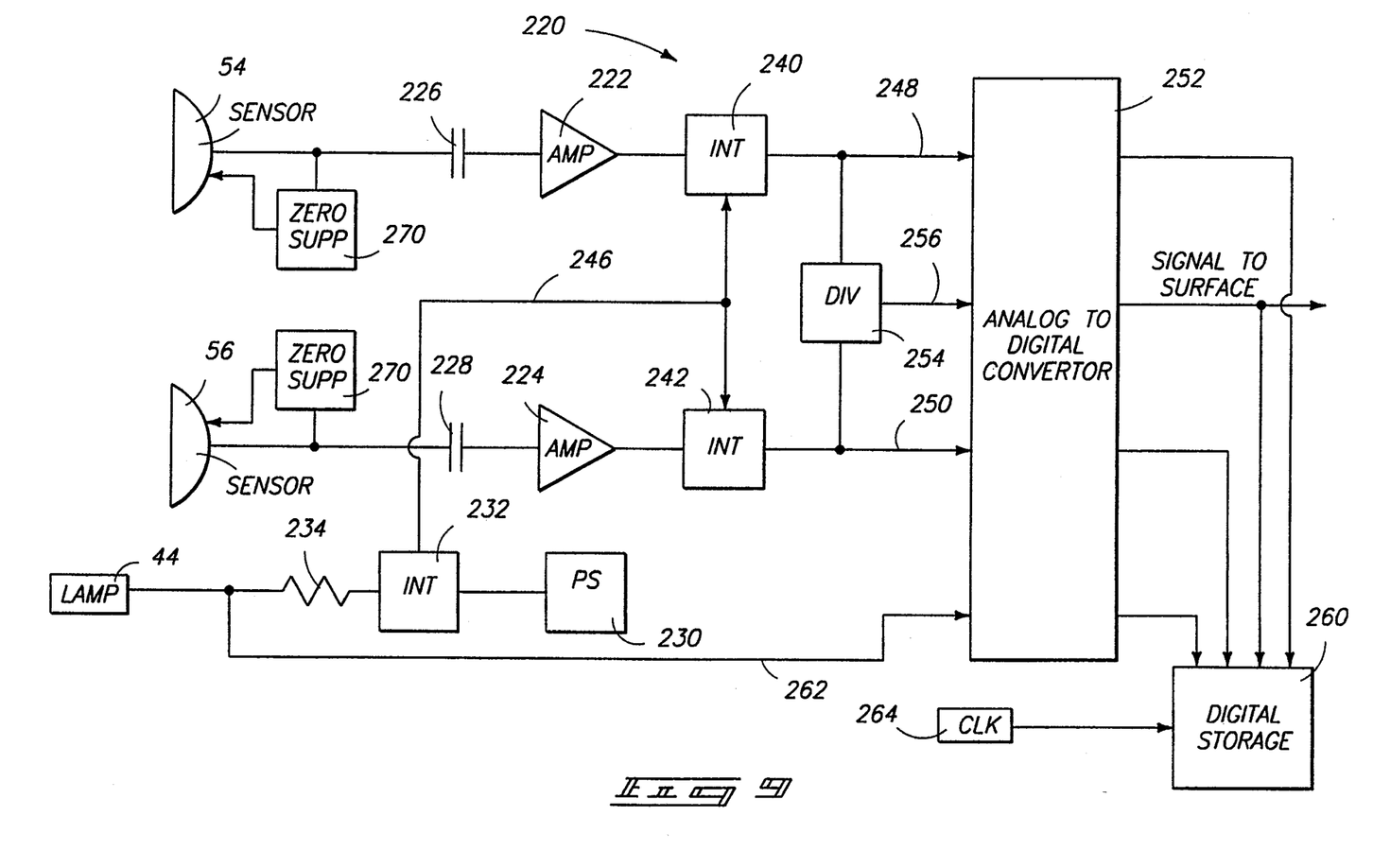
FIG. 9 is a block diagram of an electronic control system for the sub-surface exploration probe of FIG. 1.

FIG. 9 shows a preferred electronic control system 220. Sensors 54 and 56 are AC-coupled to amplifiers 222 and 224 through isolating capacitors 226 and 228, respectively. Radiant energy source 44 is connected to a lamp power supply 230 through an interrupter circuit 232. Power supply 230 is available from Baxter Scientific Products for use specifically in conjunction with its UV lamp referred to above. Interrupter circuit 232 cyclicly interrupts the connection between power supply 230 and radiant energy source 44 to provide intermittent light radiation at approximately one Hertz, as described above. A current sensing resistor 234 is connected between interrupter 232 and radiant energy source 44 to monitor the magnitude of lamp current.

The amplified signals from sensors 54 and 56, provided by amplifiers 222 and 224, are provided to a pair of "boxcar" integrators 240 and 242, respectively. A boxcar integrator such as integrator 240 or 242 accepts a gating signal and an input signal. It produces an output signal which is generally a representation of the input signal, averaged over only those time periods when the gating signal is active. In this application, boxcar integrator 240 accepts the amplified signal from sensor 54 as an input signal. It receives a gating signal 246 from interrupter circuit 232. Gating signal 246 is active only during periods of radiation emission from radiant energy source 44. Therefore, integrator 240 produces an averaged output signal 248 which represents the output or sensor 54 during periods of radiation emission. Periods when radiation emission is interrupted are ignored in forming averaged output signal 248.

Likewise, boxcar integrator 242 accepts the amplified signal from sensor 56 as an input signal. It is also connected to receive gating signal 246 from interrupter circuit 232. Integrator 242 produces an averaged output signal 250 which represents the output of sensor 56 during periods of radiation emission. Periods when radiation emission is interrupted are ignored in forming averaged output signal 250.

Averaged output signals 248 and 250 are connected to an analog-to-digital converter circuit 252. Analog-to-digital converter 252 is responsive to output signals 248 and 250 to produce digital representations of the absolute light intensity detected by sensors 54 and 56.

In addition, averaged output signals 248 and 250 are connected to an analog divider circuit 254 which produces a ratio signal 256. Ratio signal 256 is also provided to analog-to-digital converter 252 for conversion to digital format. Appropriate electrical connections are provided so that acoustic transducers of other drill string MWD components can be utilized for sending this digital data to the surface. The digital ratio signal is also provided to a digital storage memory 260 for subsequent retrieval when the drill string is raised to the surface. The absolute light intensity values are also stored in memory 260.

A current sense line 262 is connected from radiant energy source 44 to analog-to-digital converter 252. Analog-to-digital converter 252 converts the signal from current sense line 262 to digital format. The current values of radiant energy source 44 are stored at periodic intervals, signalled by a clock circuit 264, primarily to provide subsequent verification that the radiant energy source was operating during testing.

A zero suppress circuit 270 is operably connected to each of sensors 54 and 56. Zero suppress circuits 270 monitor the DC output level of sensors 54 and 56 and adjust sensor bias voltages to keep such DC levels at optimum levels for sensor accuracy.

In operation, both chemical absorption chamber 34 (including the membrane filter and screens) and the hydrocarbon solvent within the various chambers of drill collar 12 are changed at regular intervals. The modular construction of chemical absorption chamber 34 enables it to be easily replaced. Furthermore, quick-disconnect connections (not shown) are provided to allow purging of solvent within probe 10. It is also contemplated to provide electrical monitoring outputs so that an operator can monitor hydrocarbon measurements during purging. Purging will be continued as long as hydrocarbons are measured in the solvent. Depending on the source of power utilized, it may also be necessary to recharge batteries or to supply new batteries at regular intervals.

The probe operates continuously as it is lowered beneath the surface and during drilling. Solvent pump 32 slowly circulates solvent past membrane 30, through hydrocarbon detection chamber 28, and then through chemical absorption chamber 34. As the solvent passes by membrane filter 30, it contacts and dissolves hydrocarbons from the drilling fluid, carrying the dissolved hydrocarbons into hydrocarbon detection chamber 28 where fluorescent spectroscopy is performed. Hydrocarbons are subsequently removed by activated charcoal 108 in chemical absorption chamber 34.

While ethanol is preferred as a solvent in the oil-drilling environment described, other solvents will be desirable in ether environments. In some applications is may be desirable to provide additives to the solvent. These additives might produce fluorescence which is diminished by the presence of the chemical of interest. In this case, concentration determinations would be based on the amount of fluorescence intensity lost.

The measurement probe described above provides data about subsurface hydrocarbon concentrations within seconds of drill contact. Furthermore, this data is more precise than that previously available because hydrocarbons have not been diluted in the drilling fluid during a long trip to the surface. A measurement probe such as described above might be used in a variety of sub-surface applications, such as when locating buried hazardous waste or when detecting chemicals in lakes, rivers, sea waters, or groundwaters.

In compliance with the statute, the invention has been described in language more or less specific as to structural and methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents:

What is claimed is:

1. A sub-surface exploration probe for making repeated concentration measurements of a chemical occurring in a sub-surface fluid, the probe comprising:
    a probe housing having a surface which is exposed to the sub-surface fluid;
    a chemical detection chamber for containing a solvent in which the chemical is soluble;
    a filter having a first side positioned to contact the sub-surface fluid, the filter having a second side positioned to contact solvent within the housing, the filter allowing the chemical to permeate from the sub-surface fluid into solvent within the housing;
    a radiant energy source positioned relative to the chemical detection chamber to direct radiant energy into the chemical detection chamber; and
    a sensor apparatus positioned relative to the chemical detection chamber to measure radiant energy within the chemical detection chamber and thereby determine solvent chemical concentration.

2. The sub-surface exploration probe of claim 1, further comprising a mirror positioned relative to the chemical detection chamber to reflect radiant energy passing through the chemical detection chamber from the radiant energy source.

3. The sub-surface exploration probe of claim 1, further comprising a chemical absorption chamber in fluid communication with the chemical detection chamber to remove the chemical from the solvent.

4. The sub-surface exploration probe of claim 1, wherein the filter comprises at least one polymer membrane.

5. The sub-surface exploration probe of claim 1, further comprising an optical filter positioned relative to the sensor to pass radiant energy resulting from fluorescence of the chemical in the solvent, the optical filter filtering other radiant energy.

6. A sub-surface exploration probe for making repeated concentration measurements of a chemical occurring in a sub-surface fluid, the probe comprising:
   a probe housing having a surface which is exposed to the sub-surface fluid;
   a chemical detection chamber for containing a solvent in which the chemical is soluble;
   a membrane having a first surface positioned to contact the sub-surface fluid, the membrane having a second surface positioned to contact solvent within the housing, the membrane comprising a material which allows the chemical to permeate from the sub-surface fluid into solvent within the housing;
   a solvent pump to circulate solvent along the second surface of the membrane and through the chemical detection chamber;
   a radiant energy source positioned relative to the chemical detection chamber to direct radiant energy into the chemical detection chamber; and
   a sensor apparatus positioned relative to the chemical detection chamber to measure radiant energy within the chemical detection chamber and thereby determine solvent chemical concentration.

7. The sub-surface exploration probe of claim 6, further comprising a mirror positioned relative to the chemical detection chamber to reflect radiant energy passing through the chemical detection chamber from the radiant energy source.

8. The sub-surface exploration probe of claim 6, further comprising a chemical absorption chamber in fluid communication with the solvent pump and the chemical detection chamber, the solvent pump being positioned to circulate solvent through the chemical absorption chamber before circulating solvent along the inner surface of the membrane, the chemical absorption chamber containing a chemical absorption material capable of removing the chemical from solvent.

9. The sub-surface exploration probe of claim 6, wherein the membrane comprises at least one polymer membrane having a pore size of approximately 0.1 microns.

10. The sub-surface exploration probe of claim 6, further comprising at least one screen positioned adjacent the membrane first surface to protect the membrane from sub-surface materials.

11. The sub-surface exploration probe of claim 6, further comprising an optical filter positioned relative to the sensor apparatus to pass radiant energy resulting from fluorescence of the chemical in the solvent, the optical filter filtering other radiant energy.

12. The sub-surface exploration probe of claim 6, wherein the sensor apparatus comprises first and second sensors positioned relative to the chemical detection chamber to measure radiant energy of different wavelengths within the chemical detection chamber.

13. The sub-surface exploration probe of claim 6, wherein the sensor apparatus comprises:
   first and second sensors positioned relative to the chemical detection chamber to measure radiant energy within the chemical detection chamber; and
   first and second optical filters positioned relative to the first and second sensors, respectively, to filter radiant energy reaching the sensors, the optical filters having first and second center wavelengths which are different from one another, the first and second center wavelengths being selected to pass radiant energy resulting from fluoresced energy from the chemical detection chamber.

14. An in-hole oil-drilling probe which is mountable in a drill string to measure hydrocarbon concentrations in drilling fluid flowing around the drill string, the in-hole probe comprising:
   a drill collar which is mountable in the drill string, the drill collar having an outer surface which is exposed to the drilling fluid during drilling;
   a hydrocarbon detection chamber within the drill collar for containing a solvent in which the hydrocarbon is soluble;
   a membrane having an outer surface positioned to contact flowing drilling fluid, the membrane having an inner surface positioned to contact solvent within the drill collar, the membrane comprising a material which allows hydrocarbons to permeate from the drilling fluid into solvent within the drill collar;
   a solvent pump within the drill collar to circulate solvent along the inner surface of the membrane and through the hydrocarbon detection chamber;
   a radiant energy source positioned relative the hydrocarbon detection chamber to direct radiant energy into the hydrocarbon detection chamber; and
   a sensor apparatus positioned relative the hydrocarbon detection chamber to measure radiant energy from the hydrocarbon detection chamber and thereby determine solvent hydrocarbon concentration.

15. The in-hole oil-drilling probe of claim 14 further comprising a mirror positioned relative to the hydrocarbon detection chamber to reflect radiant energy passing through the hydrocarbon detection chamber from the radiant energy source.

16. The in-hole oil-drilling probe of claim 14 further comprising the solvent, the solvent comprising ethanol.

17. The in-hole oil-drilling probe of claim 14 further comprising a chemical absorption chamber in fluid communication with the solvent pump and the hydrocarbon detection chamber, the solvent pump being positioned to circulate solvent through the chemical absorption chamber before circulating the solvent along the inner surface of the membrane, the chemical absorption chamber containing a chemical absorption material capable of removing hydrocarbons from the solvent.

18. The in-hole oil-drilling probe of claim 14, the membrane comprising at least one polymer membrane having a pore size of approximately 0.1 microns.

19. The in-hole oil-drilling probe of claim 14 further comprising at least one screen positioned adjacent the membrane outer surface to protect the membrane from sub-surface materials.

20. The in-hole oil-drilling probe of claim 14 further comprising at least one optical filter positioned relative to the sensor apparatus to pass radiant energy resulting from hydrocarbon fluorescence, the filter filtering other radiant energy.

21. The in-hole oil-drilling probe of claim 14, the sensor apparatus comprising first and second sensors, the oil-drilling probe further comprising:

first and second optical filters positioned relative to the first and second sensors, respectively, to filter radiant energy reaching the first and second sensors, the optical filters passing radiant energy resulting from hydrocarbon fluorescence, the optical filters having first and second center wavelengths which are different from each other to differentiate between fluorescence of hydrocarbons originating from sub-surface fluids and hydrocarbons originating from the drilling fluid.

22. A method of measuring hydrocarbon concentrations in oil drilling fluid, the oil drilling fluid flowing around a drill collar which is mountable in a drill string, the method comprising:

contacting drilling fluid with a solvent within the drill collar to dissolve hydrocarbons from the drilling fluid into the solvent;

passing the solvent through a hydrocarbon detection chamber;

transmitting radiant energy into the solvent within the hydrocarbon detection chamber;

measuring radiant energy emanating from the solvent within the hydrocarbon detection chamber; and determining drilling fluid hydrocarbon concentration based on the measured radiant energy from the solvent.

23. The method of claim 22, further comprising circulating the solvent through a chemical absorption chamber to remove hydrocarbons from the solvent.

24. The method of claim 22, wherein the step of contacting the drilling fluid with a solvent comprises:

positioning a first side of a filter in the drill collar to contact the drilling fluid; and circulating the solvent along a second side of the filter, the filter allowing hydrocarbons to pass therethrough.

25. The method of claim 22, wherein the step of measuring radiant energy comprises measuring fluoresced light intensity from hydrocarbons in the hydrocarbon detection chamber.

26. The method of claim 22, wherein the step of measuring radiant energy comprises measuring fluoresced light intensity from hydrocarbons in the hydrocarbon detection chamber at two differing center wavelengths.

27. The method of claim 22, wherein the step of measuring radiant energy comprises measuring fluoresced light intensities from the hydrocarbons in the hydrocarbon detection chamber at two differing center wavelengths;

the step of determining drilling fluid hydrocarbon concentration comprising comparing the light intensities at the two center wavelengths to discriminate between hydrocarbons originating from sub-surface fluids and hydrocarbons originating from the drilling fluid.

* * * * *